United States Patent [19]

Hill et al.

[11] Patent Number: 5,711,935
[45] Date of Patent: Jan. 27, 1998

[54] DENTAL FLOSS

[75] Inventors: Ira D. Hill, Locust, N.J.; Michael R. Schweigert, Missouri City, Tex.

[73] Assignee: WhiteHill Oral Technologies, Inc., Hazlet, N.J.

[21] Appl. No.: 240,149

[22] Filed: May 10, 1994

[51] Int. Cl.$^6$ .................. A61C 15/00; A61C 15/04; A61K 7/16

[52] U.S. Cl. .................. 424/49; 424/50; 424/51; 424/52; 424/53; 424/54; 424/55; 424/56; 424/57; 424/58; 424/401; 156/160; 156/161; 156/169; 156/178; 433/216; 433/217.1; 523/122; 132/321; 132/323

[58] Field of Search .................. 424/401, 49–58, 424/443; 132/321, 323; 433/216, 217.1; 156/160, 161, 169, 178; 514/900, 902; 523/122

[56] References Cited

U.S. PATENT DOCUMENTS

| | | | |
|---|---|---|---|
| 3,789,858 | 2/1974 | Pesce | 132/89 |
| 4,008,727 | 2/1977 | Thornton | 132/89 |
| 4,142,538 | 3/1979 | Thornton | 132/89 |
| 4,159,619 | 7/1979 | Griset, Jr. | 28/252 |
| 4,215,478 | 8/1980 | Thomas et al. | 432/89 |
| 4,265,258 | 5/1981 | Eaton, II | 132/89 |
| 4,277,297 | 7/1981 | Thornton | 156/161 |
| 4,367,759 | 1/1983 | Kline | 132/89 |
| 4,832,063 | 5/1989 | Smole | 132/329 |
| 4,908,247 | 3/1990 | Baird et al. | 428/34.9 |
| 4,911,927 | 3/1990 | Hill et al. | 424/443 |
| 4,947,880 | 8/1990 | Tarrson et al. | 132/329 |
| 4,974,614 | 12/1990 | Selker | 132/321 |
| 5,038,805 | 8/1991 | Lee | 132/321 |
| 5,094,255 | 3/1992 | Ringle | 132/321 |
| 5,098,711 | 3/1992 | Hill et al. | 424/401 |
| 5,129,824 | 7/1992 | Keller | 433/215 |
| 5,165,913 | 11/1992 | Hill et al. | 424/49 |
| 5,183,063 | 2/1993 | Ringle et al. | 132/321 |
| 5,209,251 | 5/1993 | Curtis et al. | 132/321 |
| 5,284,169 | 2/1994 | Gilligan et al. | 132/321 |
| 5,289,836 | 3/1994 | Peng | 132/329 |
| 5,311,889 | 5/1994 | Ringle et al. | 132/321 |
| 5,311,890 | 5/1994 | Thornton | 132/329 |
| 5,316,028 | 5/1994 | Flemming | 132/329 |
| 5,518,012 | 5/1996 | Dolan et al. | 132/321 |
| 5,566,691 | 10/1996 | Dolan et al. | 132/321 |
| 5,582,194 | 12/1996 | Dolan et al. | 132/321 |

*Primary Examiner*—Gary L. Kunz
*Attorney, Agent, or Firm*—Ernest V. Linek

[57] ABSTRACT

The present invention relates to oral hygiene and specifically to an improved method for adding chemotherapeutic agents to dental floss containing several multi-fiber bundles, to methods of treating the oral cavity with the improved dental floss and to the improved dental flosses per se.

46 Claims, 1 Drawing Sheet

DENTAL FLOSS

FIELD OF THE INVENTION

The present invention relates to oral hygiene and specifically to an improved method for adding chemotherapeutic agents to dental floss containing several multi-fiber bundles, to methods of treating the oral cavity with the improved dental floss and to the improved dental flosses per se.

BACKGROUND OF THE INVENTION

Dental floss is defined in *Webster's New World Dictionary*, 1983 as "... thread for removing food particles between the teeth."

The concept of using dental floss for cleansing interproximal spaces appears to have been introduced by Parmly in 1819, *Practical Guide to the Management of Teeth*, Collins & Croft Philadelphia, Pa. Numerous types of floss were developed and used for cleaning interproximal and subgingival surfaces, until finally in 1948 Bass established the optimum characteristics of dental floss. *Dental Items of Interest*, 70, 921–34 (1948).

Bass cautioned that dental floss treated with sizing, binders and/or wax produces a "cord" effect as distinguished from the desired "spread filament effect." This cord effect reduces flossing efficiency dramatically and virtually eliminates splaying (i.e., the flattening and spreading out of filaments) necessary to achieve the required interproximal and subgingival mechanical cleaning. This cleaning is then required to be followed by the entrapment and removal of debris, plaque and microscopic materials from interproximal spaces by the "spent" floss as it is removed from between teeth.

Three basic nylon fiber bundle constructions have been previously approved by the Food and Drug Administration (FDA) which has classified floss as a medical device. The three basic constructions are: 140 denier (68 filament), 100 denier (34 filament) and 70 denier (34 filament). Heretofore, 6 to 10 bundles of these three types were twisted together along with bonding agents to produce various commercial dental flosses.

Proper use of dental floss is necessary to clean the considerable surface area on the interproximal surfaces of teeth, which cannot usually be reached by other cleaning methods or agents, e.g., the bristles of a toothbrush, the swishing action of a rinse, or by the pulsating stream from an oral irrigator.

Historically, the purpose of dental floss was to:
1. dislodge and remove any decomposing food material, debris, etc., that has accumulated at the interproximal surfaces, which could not be removed by other oral hygiene means, and
2. dislodge and remove as much as possible the growth of bacterial material (plaque, tartar, calculus) that had accumulated there since the previous cleaning.

The commercialization of the innovative dental flosses described and claimed in U.S. Pat. Nos. 4,911,927; 5,098,771 and 5,165,913 to Hill et al. has extended the purpose of dental floss to include the release therefrom of chemotherapeutic agents, both interproximally and subgingivally. The efficacy of these new dental flosses has been documented in clinical studies reported in a filing responsive to the FDA call-for-data of Sep. 19, 1990, 55 Fed. Reg. 38560. See Docket No. 81N-0033, OTC 210246 to 210262. The Hill et al. patents and the referenced clinical studies are hereby incorporated herein by reference.

While the flosses described and claimed in the Hill et al. patents are quite good, improvements are always possible. Thus, the present invention represents an improved version of the dental flosses disclosed and claimed in aforementioned Hill et al. patents, whereby improved cleaning, treating and/or removing of debris, etc. from interproximal and subgingival areas can be easily conducted while maintaining floss integrity.

SUMMARY OF THE INVENTION

The present invention is based upon the discovery that multi-fiber dental flosses "loaded" with chemotherapeutic agents such as those described and claimed in U.S. Pat. Nos. 4,912,927; 5,098,711 and 5,165,913 can be improved by expanding the interstitial space between the fibers and by introducing the various chemotherapeutic preparations into said expanded interstitial space. In the present invention, these improvements in multi-fiber dental flosses are achieved while maintaining dental floss integrity.

The improved multi-fiber, multi-bundle, dental flosses of the present invention, with their expanded interstitial spaces, are particularly adaptive to working between the teeth, i.e., in the interproximal spaces as well as below the gingival margin. This adaptability of the present dental floss can be enhanced by various bulking processes, fiber construction, choice of filaments and/or the addition of various chemotherapeutic agents.

Generally, these improved multi-fiber dental flosses with expanded interstitial space can be loaded with more chemotherapeutic agents, at faster loading speeds and at lower loading temperatures, than possible for the previously known flosses of Hill et al. The improved flosses of the present invention also possess improved dental floss integrity in comparison with the previously known flosses of Hill et al.

Various commercial processes previously employed for use in "bulking" yarns have been found suitable for expanding the interstitial space between the multi-fibers in the several bundles that comprise the dental flosses of the present invention.

Of the various bulking processes used with various filament yarns, texturizing is believed to be the most adaptable and suitable for the multi-fiber bundles of the present invention. False twist texturizing in combination with air entangling and twisting is particularly preferred.

Texturizing is the means whereby stretch, bulk, greater absorbency and improved hand are combined with continuous filament nylon through the permanent introduction of crimps, loops, coils or crinkles into otherwise smooth continuous filaments. The success of most texturizing processes with the exception of air-texturized yarns, depends on the thermoplasticity of nylon and its ability to be deformed, heat-set and developed. See *Textured Yarn Technology*, Vol. 1, Monsanto, pp. 3–4 (1967), the entire disclosure of which is hereby incorporated herein by reference.

There are various methods of texturizing yarns well known to those skilled in textile arts. Most, if not all of these, as well as variants which have no great textile advantages but will affect the properties of a dental floss, particularly for delivering chemotherapeutic preparations, are suitable for the purposes of this invention. The textile industry commercially utilizes three distinct categories of texturizing suitable for use with the present invention: stretch, modified stretch and bulk, ibid, p. 7.

The stretch yarns include: conventional twist-heat set, untwist batch processes yarns, false twist yarns, and crimped yarns.

The modified stretch yarns include: Helanca, overfeeding-heat zone stabilizing yarns; and autoclaved or dyed soft yarns.

Bulk yarns include: crimp type produced by stuffer box methods; loop-type produced by air texturizing; crinkle-type produced by knit-deknit process or by gear crimping and twisted textured yards such as Turbo Duotwist textured yarns that are classified, e.g., Mylast, Cumuloft, etc. See Table 1.3, *The Monsanto Guide to Textured Blue "C" Nylon Yarns*, ibid.

When one or more texturizing processes (e.g., double crimping) are employed in the manufacture of the dental flosses of the present invention, in addition to expanding the interstitial space between fibers so that more chemotherapeutic agents can be introduced into the extended space available, they generally also impart a "memory" to the fibers in the bundle. That is, when the binding of the chemotherapeutic agents to the fibers is disrupted i.e., by solution of the agents by saliva and/or sulcal fluids or by the addition and release of strain to the floss such as occurs during the flossing process, this "memory" is "activated" and the multi-fiber floss assumes a "bulkier" i.e., more expanded texturized form. This unexpected increase in dental floss multi-fiber bundle bulk offers numerous advantages and improvements over previously known dental flosses including those disclosed and claimed in the referenced patents to Hill et al. These advantages range from improved flossing, i.e., improved mechanical cleaning, as well as improved release of chemotherapeutic agents, to possible new uses for dental floss heretofore unavailable, such as aspirating infected interproximal sites, evacuating infection discharge, etc., from interproximal areas.

In particular, the improved multi-fiber dental flosses of the present invention are deemed to be "activated" (see definition below) and as such are easily slipped between the teeth with minimal fraying, shredding, breaking and/or snagging. Thereafter during flossing, the floss spreads out to optimize chemotherapeutic agent release, mechanical cleaning, the take-up and removal of debris, the loosening of cellular material, plaque, tartar, calculus, gum disease discharge toxins, and the like. See FIGS. 1-3 accompanying this specification.

As used herein the term "activation" (or related terms), describes the easy separation of the individually coated filaments or fibers (each of which are coated with chemotherapeutic agent(s)) from each other, thereby creating a multitude of temporary floss structures where the openings in the interstitial space is substantially greater than before "activation." This expansion or separation is a function of the "memory" of the textured polymer filaments and is retained during the process described herein for loading the chemotherapeutic preparations. The benefit of the "activation," above and beyond that inherent in the improved loading properties include: (a) greater access of the sulcal fluids to the chemotherapeutic preparations, (b) greater accessible surface area for release of these chemotherapeutic preparations and (c) greater cleaning of debris from the interproximal areas of the teeth and subgingival margins.

The "activation" of the floss of the present invention can be easily seen when readying the floss for use by wrapping a convenient length around each of the forefingers, applying tension of the sort required for insertion between the teeth and then releasing said tension. Upon release, the floss of the present invention, unlike any other floss known to the present inventors, expands to a much bulkier state, i.e., at least 2×, preferably at least 5× (and even higher), than before applying and releasing the tension.

A similar "activation" or opening of the interstitial floss fiber spaces occurs during the normal use of the floss, i.e., in the interproximal areas of the teeth as the tension used to pass the floss between the teeth is applied and relaxed (loosened) during the flossing process. See FIGS. 1-3 accompanying this specification.

The terms fiber and filament are used synonymously throughout this specification in a manner consistent with the first three definitions of "fiber" and the first definition of "filament" as given in the *New Illustrated Webster's Dictionary*, ©1992 by J. G. Ferguson Publishing Co. the relevant disclosure of which is hereby incorporated herein by reference.

BRIEF DESCRIPTION OF THE DRAWINGS

Referring to FIGS. 1-3 of the drawings:

Referring to FIGS. 4-6 of the drawings:

DETAILED DESCRIPTION OF THE PREFERRED EMBODIMENTS

Dental flosses comprising several multi-fiber bundles containing chemotherapeutic agents such as those described in U.S. Pat. Nos. 4,911,927; 5,098,711 and 5,165,913 can be improved by expanding the interstitial space around the fibers, so long as these multi-fiber dental flosses (now with expanded interstitial space) maintain dental floss integrity, which is required for effective use.

Most commercial processes used for bulking yarns have been found suitable for extending or expanding the interstitial space between fibers of the bundles of multi-fibers that make up the dental flosses of the present invention. These yarn bulking processes are generally described as texturizing or bulking processes. The net effect of these expansion processes is to permanently increase the space around the multi-fibers in each bundle while generally introducing a "memory" to these fibers with expanded interstitial space, such that these texturized fiber bundles are prone to return to their texturized or bulked form when "activated," as that term is defined above. Some of the suppliers of various commercial texturized and/or bulked fibers suitable for the purposes of the present invention are detailed at pp. 567–483, in Monsanto's *Texturized Yarn Technology*, Vol. 1 (1967).

Chemotherapeutic agents are introduced into the expanded interstitial space produced by texturizing and/or bulking of bundles of multi-fiber dental floss. Means for introducing these agents into the extended interstitial spaces are described in U.S. Pat. Nos. 4,911,927; 5,098,711 and 5,165,913 and these processes are hereby incorporated herein by reference.

Generally, it has been found that these expanded interstitial space, multi-fiber dental flosses can be loaded with more chemotherapeutic agents, at faster loading speeds, and at lower temperatures, than previously known flosses, including those described in the Hill et al patents. See the Examples set forth below.

A review of the construction of the preferred dental floss used in the method of the present invention shows that the chemotherapeutic substances in various carriers including the melt emulsion carriers employed by Hill et al. are contained essentially in the interstitial spaces between the multi-fiber bundles that comprise the dental floss with minimum chemotherapeutic agent/melt emulsion on the outer surface of the expanded dental floss. The internal loading of these compositions is achieved by repetitively spreading and compressing said fibers by repetitively passing the floss over a series of flat surfaces under tension and through compressing means as described in the referenced Hill et al. floss patents.

It is most unexpected and unobvious that the interstitial space between the multi-fibers in the multi-fiber bundles that make up the dental flosses of the present invention can be expanded along with imparting "memory" to the textured fiber bundles, while maintaining dental floss integrity. In other words, one would ordinarily expect the resultant expanded interstitial space dental floss to be less effective for flossing, particularly with respect to fitting between teeth, fraying, shredding, breaking and/or snagging. Surprisingly, the dental flosses of the present invention maintain floss integrity and are generally considered superior to traditional dental flosses and to the dental flosses disclosed and claimed in the Hill et al. patents.

Surprisingly, it was found that the expanded interstitial space, multi-fiber dental flosses of the present invention:
1. slip easily between teeth with minimal snagging, shredding, fraying and/or breaking;
2. exhibit unprecedented splaying and release interproximally & subgingivally of chemotherapeutic agents, and
3. effectively entrap and remove debris, food particles, loosened plaque, tartar and cellular material from interproximal & subginival areas, etc.

The multi-fiber bundles that comprise the dental flosses of the present invention which have undergone one of the various bulking processes such as one of the many texturing processes described above, in addition to bulking-up, as noted previously acquire a memory which unexpectedly can be called into play, i.e., "activated," after the chemotherapeutic agent has been introduced into the textured floss. This "activation" can be effected by simply placing a strain on a section of floss followed by a relaxing of the strain. Upon relaxing the strain, the "activated" dental floss immediately expands to fluffy bundles of fibers several times larger (2×, 5×, etc.) than the diameter of the dental floss prior to "activation."

Figure 1:
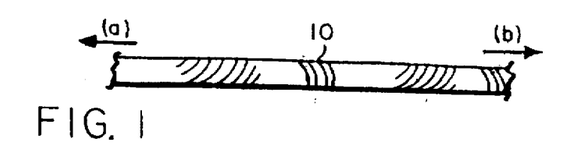
FIG. 1 is a plan view illustrating a striped, multiple-bundle, multi-fiber version of the dental floss 10 of the present invention, containing one or more chemotherapeutic agents, prior to being activated by the process of being pulled (stressed) in opposite directions as indicated by opposing arrows a & b.
Figure 2:
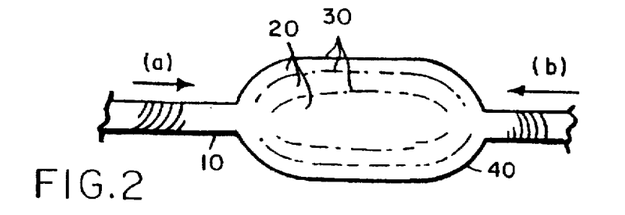
FIG. 2 is a plan view illustrating a striped, multi-bundle, multi-fiber version of "activated" dental floss 10 of the present invention, containing one or more chemotherapeutic agents, and wherein the interstitial space 20, between multi-fiber 30 has been expanded to create fluffy bundles of fibers 40, fibers 30 has expanded to create fluffy bundles of fibers 40, several times (2×, 5×, etc.) the diameter of the dental floss 10 prior to activation. This expansion is introduced by relaxing the strain previously placed on the dental floss as shown by arrows a & b.
Figure 3:
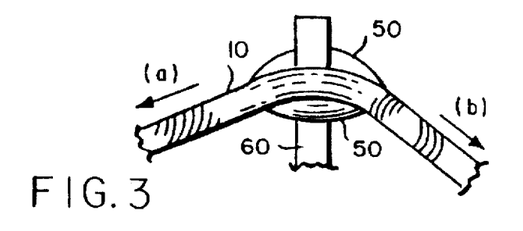
FIG. 3 is a plan view illustrating the splaying property, 50, of the activated multi-bundle, multi-fiber dental floss 10 of the present invention. The splaying is achieved by drawing the activated dental floss over (or between) a hard surface 60 (e.g., a tooth or teeth), as indicated by arrows A & B.

Additionally, the "activated" dental floss spreads out wider than other flosses when stretched and passed over a hard surface under comparable force conditions. These unique "activation" and splaying features are illustrated in FIGS. 1–3 of the drawings.

This unobvious and unexpected propensity of the dental floss of the present invention to expand dramatically upon the application and release of a strain (such as encountered when working the floss between the teeth) followed by the propensity to spread out (splay) substantially more than other flosses, is most unique and readily distinguishes the flosses of the present invention from all other known dental flosses.

According to published reports, mechanical texturing creates an asymmetric distribution of tensile forces in the filaments of the bundle, generally by subjecting one side of each filament to a greater tension than the other. The mechanical deformation is applied to the bundle at a temperature at which the polymer segments have sufficient mobility to change their orientation in the time scale of the process. This stabilizes the deformed configuration, making it permanent, i.e., the filaments have a "memory" for the deformed state. See, *American Dyestuff Reporter*, 55, (6) 37–43 (1966). Thus, the net effect of texturizing is to create a memory in the fiber bundle for the deformed state.

Figure 4:
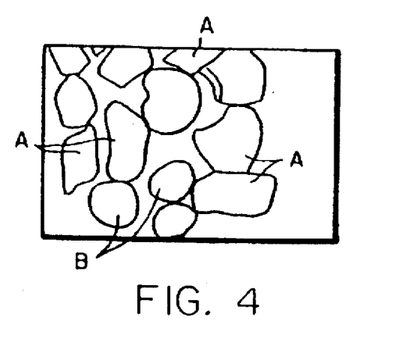
FIG. 4 illustrates a photomicrograph of part of a cross-section of a false-twist type stretch nylon 6,6 bundle. The polygon-shaped filament cross-sections, A, resulting from the twist being incorporated into the bundle while it was deformable during its passage over a heating means can be compared to the non deformed generally spherical filaments B.
Figure 5:
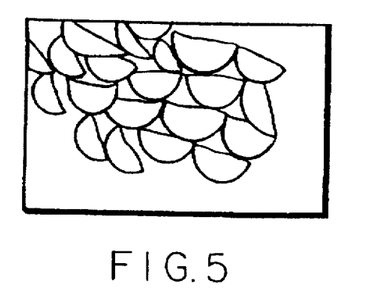
FIG. 5 illustrates a photomicrograph of part of a cross-section of an edge-crimped nylon 6,6 fiber bundle. The flattened filament cross-sections, A, are formed by passing the heated bundle over a dull knife edge.

The filaments to be texturized are crystalline and can be deformed when there is at least a partial melting and recrystallization which can take place below the melting point. This is illustrated in FIGS. 4 and 5 accompanying this specification, which are illustrations of cross-sectional views of partial bundles of filaments that have undergone different types of texturizing which resulted in importing "memory" to the filaments.

The resistance of a yarn to simple tension applied in one direction only, is known as tensile stress. The resultant elongation or extension is known as strain. The general stress-strain behavior of the multi-bundle, multi-fiber dental floss with expanded interstitial space containing chemotherapeutic preparations in said space, distinguishes this dental floss from all other commercial dental flosses including those described and claimed in the referenced U.S. Patents to Hill et al.

Figure 6:
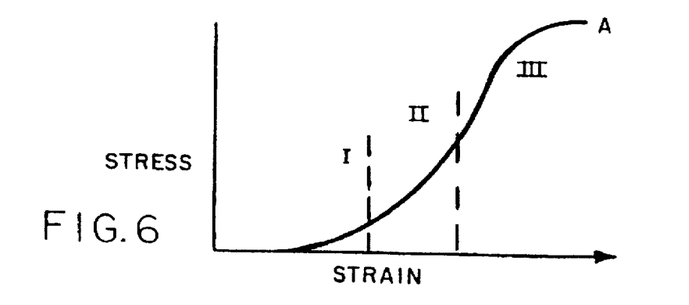
FIG. 6 illustrates a typical stress, strain curve for the multi-bundle, multi-fiber texturized dental floss the present invention with the three distinct regions designated I, II & III respectively.

The general stress-strain of the multi-bundle, multi-fiber dental flosses of the present invention during the "activation" phase is illustrated in FIG. 6. The stress-strain response is characterized by three separate regions. The first region, (I) is the stretch region where straightening of the texture or uncrimping occurs. In the second region, (II) additional uncrimping plus initial bundle elongation occurs. The third region, (III) represents bundle elongation only. The fully extended terminal point, A, represents the crimp removed condition, i.e., the point at which the bundle looks more like an unmodified continuous filament bundle. Upon relaxing the stress-strain force, the multi-bundle, multi-fiber floss immediately expands to several times the "preactivation" diameter.

Surprisingly, the introduction of stress/strain to the multi-bundle, multi-fiber dental floss prior to flossing, not only results in the unexpected expansion of the dental floss with more pronounced splaying as discussed above, but also prepares the optional carrier and chemotherapeutic preparation for release interproximally during flossing. It has been observed that denier and filament count effect the stress/strain performance, i.e., generally, the lower the total denier the fewer the number of filaments, the greater the stretch potential.

The chemotherapeutic preparations introduced into the expanded interstitial space of the multi-bundle, multi-fiber dental flosses of the present invention are released into the oral cavity during flossing. Most of this release of chemotherapeutic preparations takes place interproximally and/or in the subgingival margin. The pressures and forces encountered during flossing allow for these chemotherapeutic preparations to be progressively released interproximally and under the gum line. As this dental floss is worked through a contact point and moved gently under the gum line the chemotherapeutic preparations are continually released into those areas of the gum/tooth interface where plaque, debris and infection are difficult to clean, remove and treat, respectively. Suitable formulations for some of these various chemotherapeutic agents are described in U.S. Pat. No. 5,098,711 to Hill et al. and are incorporated herein by reference. See the various Examples and Tables I through XI of the Hill et al. patent.

A review of the construction of the multi-bundle, multi-fiber, expanded interstitial space, dental floss of the present invention shows that the chemotherapeutic compositions of the present invention are contained essentially in the interstitial spaces (which have been expanded) between the fibers of the floss, with minimum levels of chemotherapeutic preparation(s) on the outer surface of the floss. This internal loading of these chemotherapeutic preparations is achieved by repetitively spreading out and compressing the multi-fibers during manufacturing while simultaneously introducing the chemotherapeutic preparation(s) contained in an appropriate carrier, into the expanded spaces around the opened and/or compressed fibers. This manufacturing process is described in detail in U.S. Pat. No. 4,911,927 to Hill et al. and is hereby incorportion The application of the dental flosses of the present invention to oral hygiene range from: cleaning interproximal and subgingival areas, to removing plaque, tartar and calculus from these areas, to the treatment of various conditions ranging from gingivitis to gum disease by the interproximal release of various medicaments etc. These applications are described in detail below.

A healthy gingival architecture is characterized by a sulcus of 1 to 3 mm in depth, as measured between the crown of the tooth and the surrounding gingival tissue. Healthy gingiva appears pink, with a firm, stippled surface, and it does not bleed either by mild provocation or spontaneously, and is not painful. The gingival sulcus of a health periodontium has low numbers of principally facultative of microaerophilic, gram-positive, non-motile organisms and low numbers of neutrophils.

Periodontal disease is a term used to collectively designate several specific diseases of the gingiva (gingivitis) and of the tissues supporting the teeth (periodontitis). Organisms which grow in the microenvironment of the periodontal pocket are implied as the cause of these periodontal diseases. As the disease becomes established, major changes occur in this environment. It becomes more anaerobic, populated by Gram-negative, often motile organisms and frequently, intermittently infused with large numbers of neutrophils. The environment becomes perfused by an increasing flow of gingival crevice fluid (GCF), the primary aqueous milieu of the periodontal microenvironment.

Alterations of the gingiva seen with gingivitis are principally those associated with inflammation. Gingiva appear red, swollen and bleed easily. This condition is often associated with large numbers of spirochetes and renders the gum tissue painful to touch or probe, and is frequently associated with halitosis. The most common form of gingivitis is due to accumulation of supragingival bacterial plaque and as such is treatable by the chemotherapeutic flosses of the present invention.

Periodontitis is a destructive form of periodontal disease. This condition results in the loss of bone and collagen support of affected teeth. Periodontitis is the result of local infection by specific microorganisms or groups of microorganisms and as such should be amenable to antibacterial therapy such as treatment with the chemotherapeutic flosses of the present invention.

It has been established that even though certain antimicrobials such as $SnF_2$, chlorohexidines, etc. are effective in killing periodontal microorganisms at concentrations commonly used in mouth rinse preparations, delivery as a mouth rinse is inadequate for the treatment of periodontitis. The rinse does not reach the periodontal pocket nor the interproximal sites of infection.

The release of the various chemotherapeutic preparations from the floss of the invention subgingivally and interproximally in combination with the unique mechanical action of the floss of the invention offers a new chemo/mechanical therapy to aid in the treatment of less severe sites of periodontitis. In deep periodontal pockets, i.e., 5 to 10 mm deep, the preferred chemotherapeutic flosses of the present invention have lesser effect since infection in pockets of this depth is inaccessible to flossing and serves as a reservoir for reinfection. When surgery and other treatments are used for these conditions these flosses show promise as maintenance products.

In addition to the anticaries, gingivitis and periodontal treatments discussed above there are additional antimicrobial treatments for specific conditions that lend themselves to the chemotherapeutic flosses of the invention. One application is the pretreatment of patients for whom oral surgical procedures are planned. It has long been recognized that any form of dental therapy which creates a laceration of the gingiva produces transient bacteremia. Therefore it is believed that any reduction of intraoral organisms such as S. mutans with, for example, an $SnF_2$ containing floss, prior to surgical procedures would be helpful. It is noted that S. mutans is also associated with endocarditis.

A second situation in which reduction of bacterial numbers would provide therapeutic benefit is the surgical post operative maintenance phase. During this period of wound healing, surgical results would be improved by controlling plaque, S. mutans, etc. with, for example, an $SnF_2$ containing floss.

The chemotherapeutic flosses of the present invention offer a new treatment for plaque control and for gingivitis control. As noted above the alterations of the gingiva seen with gingivitis are principally those associated with inflammation by specific microorganisms or groups of microorganisms. It has been established that this disease is amenable to antibacterial therapy. However, control of this disease is not so much a problem of killing pathogens as it is of altering local microbial ecology. This control of the microbial ecology is achieved by:

a. regular disruption of the subgingival microflora, and
  b. disruption or preferably, removal of the supragingival plaque.

It has been observed that gingivitis is a localized condition that is responsive to treatment with the flosses of the present invention (in particular, $SnF_2$ floss). The release of $SnF_2$ preparations into "localized" inflammations and gingival eruptions delivers higher concentrations of antimicrobial $SnF_2$, interproximally than achievable with any other $SnF_2$ products such as rinses, gels, dentifrices, etc. This localized delivery of $SnF_2$ disrupts the local microbial ecology sufficiently to control the infection. Once disrupted, reorganization of the complex gingivitis ecosystem present at a colonization site requires time. It has been found that repeated disruptions via regular flossing prevents such reorganization and is an effective means of controlling the local microbial ecology including *S. mutans*.

Colonization of tooth surfaces by *S. mutans* is not uniform throughout the mouth but instead is highly localized to specific tooth surfaces. As a result, dental caries activity is not uniformly distributed but tends to develop between the teeth, around the necks of teeth, and in fissures of the occlusal surfaces. Therefore, treatments localized to specific tooth surfaces with the $SnF_2$ floss are proposed. The resultant efficient delivery of $SnF_2$ in the preparations released from the floss; coupled with the mechanical cleaning of localized tooth surfaces promises superior anticaries clinical effectiveness.

It seems likely that such localized approaches which could affect individual lesions or individual tooth areas could have widespread applicability. For example:

a. The application of orthodontic appliances creates new areas for dental plaque accumulation and constitutes a serious home care problem. The regular use of $SnF_2$ floss as part of orthodontic appliance use could reduce the iatrogenic disease liability of these appliances;

b. Mechanically sound dental fillings are commonly replaced due to deterioration of their margins which allow bacterial access to tooth structure and recurrent decay. *S. mutans* colonization accelerates at interproximal restorations (1983). Each replacement enlarges the cavity and thereby structurally weakens the tooth. The regular use of $SnF_2$ floss could extend the longevity of such fillings and maintain a substantially caries free condition, especially at interproximal restorations; and c. Radiotherapy patients experience accelerated caries which should be treatable with more frequent flossing with the $SnF_2$ floss.

Bacteria have been found to attach to oral tissue with a remarkable degree of specificity. This attachment appears to be the first step in the colonization process. It is reported that low levels of tetracycline applied topically affects the adhesion of suspected periodontal pathogens.

In shallow periodontal pockets, i.e., those no greater than about 3 mm in depth, local periodontitis conditions of patients should improve with regular use of the tetracycline in the load of the floss. One would expect such treatment to dramatically change the periodontal microflora and to rapidly decrease clinical signs of gingival inflammation. When tetracycline is added to the floss in concentrations ranging from between about 60 µg/yd to about 10 mg/yd, the pathogenic microflora of the tetracycline released for each interproximal surface flossed is between about 1 mg and about 10 mg, with total release for all 60 surfaces requiring at least about 64 mg/yd.

The topical application of various antibiotics to interproximal sites as well as subgingivally is preferred over "systemic" treatments with those substances. That is, the risk of adverse side reactions to the patient which accompanies most ingested systemic antimicrobials is reduced substantially. In addition, application of the antimicrobial to specific infected areas can be achieved with a higher frequency, topically than systemically. This assures higher antibiotic concentrations at the site(s) of infections and a higher incidence of effectiveness in a shorter period of time.

Since plaque is regarded by most of the dental professionals as a causative agent leading to various dental pathologies discussed in detail below, there is considerable desire by most consumers to remove or prevent the formation of plaque on a daily basis.

Most authorities agree that control of periodontal diseases requires:

1. regular disruption of subgingival microflora, and
2. regular removal of supragingival plaque.

There are four oral care techniques which address the problem of plaque:

A. Abrasive removal of the plaque film,
B. Antimicrobial action,
C. Removal of plaque precursors, and
D. Altering the attachment of plaque.

All of the foregoing are achieved with various chemotherapeutic preparations contained in the multi-fiber, expanded interstitial space flosses of the present invention. These are discussed in detail in the U.S. Pat. No. 4,911,927 to Hill et al. and that discussion is hereby incorporated herein by reference.

The unique expanded construction of the dental flosses of the present invention offer interproximal and subgingival treatment opportunities for diseased infected, bleeding and/or traumatized gum conditions that were unavailable heretofore. For example:

a. "activating" a dental floss comprising several multi-fiber bundles, containing cleaners and adsorbents; working said "activated" dental floss interproximally and subgingivally to release said cleaners and adsorbents and removing the spent dental floss along with entrapped debris, bacteria, bacteria ladened fluids, toxins, etc.

b. "activating" a second dental floss comprising several multi-fiber bundles containing chemical aspirants, working said "activated" floss subgingivally and interproximally to aspirate sites of infection, disease, bleeding etc and removing the spent dental floss along with entrapped debris, aspirated bacteria, bacteria ladened fluids, toxins, etc.; and c. "activating" a third dental floss comprising several multi fiber bundles containing appropriate chemotherapeutic preparations selected from the group consisting of: antimicrobials, antibiotics, healants, soothants, oxygenating compounds and antibacterial agents.

The opportunity to chemically aspirate interproximal and subgingival sites of infection and/or to draw out and remove the bacteria, fluids debris, etc. from these sites by means of some multi-fiber interproximal delivery vehicle opens a whole new site-specific treatment approach for such infections and disruptions. These new interproximal and subgingival treatments are particularly helpful as pre- and post-treatments for oral surgery patients, as treatments for rampant caries in radiotherapy patients, as an at-home regimen for treating periodontitis and as a two and/or three times a day treatment of oral lesions, etc. characteristic of advanced stage AIDS patients.

Virtually all natural and man-made fibers and specifically filament yarns, twisted continuous filament yarns and the like can be texturized, including: nylon, polyester, polypropylene and various blends of such fibers and/or filaments. Texturizing can be achieved with false twist, core-bulked, textralized, edge crimping, gear crimped, air jet, crinkle, cotexturizing, etc. type processes or modifications thereof as described in E. Stacy, *Hosiery Res. Bull*, (1): 1–22, 1957 and the references cited at pp. 20–22 of *Textured Yarn Technology*, Vol. 1, Monsanto, 1967. See also *Textured Yarns*, Monsanto, 1962 and *Stretch Woven Fabrics and Textured Yarns*, Monsanto 1963.

These "bulking" processes can be carried out with various types of texturizing equipment as described at pp. 223–233 of *Textured Yarn Technology*, Vol. 1, Monsanto, 1967, including for instance: Hobnourn No. 2086, ARCT: FT-V, FT-1, FT-F, FT-3, FT-400, FT-U and FT-415; Carolina UNRAV Purdy-Hodges Yarn Crimper, Whitlin RD-5; U.S. Acme Jumbo & Model I Texturizers; Fujiloft F205 Heberlein High Performance Universal Texturizing Machine, Autotwister TZ21, False Twister F231, Ratti Model TRS, Berliner SDD-Set 280, Two-For-One Twister; Turbo-Twist, Pinion & Turbo-Duo Twist.

The equipment and processes used for texturizing are described in numerous U.S. Patents and literature as set forth below, the disclosures of which are hereby incorporated by reference into this specification:

U.S. Pat. Nos. 2,463,620; 2,655,781; 2,463,618; 2,904, 952; 2,803,105; 2,803,108; and 2,803,109.

"A survey of the literature and patents relating to Bulked Continuous-Filament Yarns", E. Hutton and W. J. Morris, The Cotton Silk and Man-Made Fibres Research Assoc., Shirley Inst. Didsbury, Manchester, England (1963).

"Bulk, Stretch and Texture", The Textile Inst., Manchester England 1966 and the various references cited at pp. 97–104 of *Textured Yarn Technology*, Vol. 1; Monsanto, 1967.

U.S. Pat. Nos. 2,790,611; 2,919,534, 2,921,358, 2,925, 641; 2,931,089, 2,977,661; 2,997,746; 2,977,663; 3,017,684; 3,021,588; 3,025,584; 3,028,653; 3,028, 654; 3,035,328; and 3,047,932; British Patent Nos. 722,756; 761,084; 801;147; 802,689; and 839,393.

See also yarns and equipment described at pp. 204–234 in *Textured Yarn Technology*, Monsanto, Vol. 1 1967.

See also U.S. Pat. Nos. Re. 23,824; 2,575,837; 2,505,618; 2,514,557; 2,575,781; 2,575,833; 2,575,837; 2,575, 838; 2,575,839; 2,647,285; 2,734,228; 2,734,229; 2,734,251; 2,734,252; 2,740,992; 2,758,357; 2,758, 358; 2,760,252; 2,854,701; 2,854,728; 2,854,729; 2,960,729; 2,960,730; 2,997,747; 3,000,059; 3,000, 060; 3,016,677; 3,027,108; 2,783,609; 2,852,906; 2,868,967; 2,958,112; 2,994,938; 3,013,379; 3,017, 737; 3,043,088; and 3,091,908.

Nylon is the preferred general purpose filament due to its strength, tenacity and workability. Particularly preferred is partially oriented nylon texturized with a false twist-air entangled/twist, combination as described in greater detail in the examples provided below. Additionally, Monsanto's high tenacity continuous filament nylon is also suitable. See also "Elements of the False Twist Stretch yarn Process", pp. 52–58, *Textured Yarn Technology*, Vol. 1, Monsanto, 1967.

The influence of setting nylon filaments in a helical shape is discussed by J. J. Mertens, *Bulk Stretch & Texture:*, The Textile Institute, 1966 and by M. J. Denton, *J. Textile Inst.*, 57, 1265 (1969), the disclosures of which are hereby incorporated herein by reference.

It has been observed that the specific chemotherapeutic agent load capacity of the multi-fiber "activated" dental flosses of the present invention are from about 25% to over 100% greater than that of dental flosses that have not been exposed to an interstitial space expanding process such as texturizing, when both are loaded under comparable conditions. See Examples 1–4 below.

Similarly, the percent of chemotherapeutic agent load that is releasable during flossing is also higher in the flosses of the present invention. The dental flosses produced by the method of this invention exhibit improved splaying, superior interproximal coverage with improved flossing performance, particularly in areas such as breaking, fraying, snagging, etc.

These performance superiorities are evident even when the load is maintained at equal or lesser quantities than described in U.S. Pat. No. 5,165,913 to Hill et al. For certain applications, the ability to provide a wide range of loading while maintaining the other improvements as well, will be evident to one skilled in the art of oral care in general and gum disease in particular.

The dental floss used in the method of the present invention preferably comprises:

1. a bundle of multi-fiber dental floss containing a chemotherapeutic agent wherein:
   a. the multi-fiber dental floss:
      1. contains from between 2 and 12 bundles,
      2. has a denier between about 300 and about 1,200, and
      3. contains between about 100 and about 800 filaments;
   b. the fibers include natural and/or man made fibers and mixtures thereof including filament bundles and twisted continuous filament bundles including nylon, polyester, polypropylene, cotton, silk, etc., and blends thereof. Of particular value are bi-polymer fibers spun from distinct, unblended polymers in a manner which causes the opposing halves of the filament cross-section to exhibit different stretch and texturizing properties thus developing remarkably complex interstitial spaces while retaining the tenacity and strength properties of the nylon half.
2. Bundles of multi-fiber dental floss as described above, containing a chemotherapeutic preparation and/or other multi-fibers with specific functionality such as adsorption wherein:
   (a) the multi-fiber, multi-composition dental floss:
      1. contains 1–6 bundles of the specific functionality fibers,
      2. has a specific functionality fiber denier between 50 and 500, which
      3. contains between 20 to 400 filaments.
   (b) the multi-composition portion of the multi-fiber dental floss includes:
      1. swellable fibers such as used in disposable diapers;
      2. saliva or water soluble fibers containing additional chemotherapeutic preparations,
      3. hollow membrane transport fibers such as are used in dialysis systems,
      4. microporous fibers such as the Accurel® fibers by AKZO Chemie constructed from polyethylene or polypropylene,
      5. fibers rendered essentially microporous by the incorporation of micron-sized particles of calcium carbonate, talc, etc.,
      6. fibers capable of withdrawing water or specific fluids by incorporating micron-sized particles of agents such as calcium chloride, silica gel, activated charcoal and the like and, 7. flat fibers or thin flat ribbons of teflon or teflon-like structures such Gore-Tex® which serve to guide the textured, loaded fibers easily to the interproximal, subgingival sites.

In a preferred embodiment of the present invention the multi-fiber dental floss used is nylon which contains between 4 and 8 bundles with a denier between about 500 and about 1,000 and contains between about 200 and 600 filaments.

In a particularly preferred embodiment of the present invention the dental floss used is nylon containing 6 bundles has a denier of about 840 and has approximately 408 filaments.

Chemotherapeutic preparations suitable for introduction into the expanded interstitial space available in the bulked, multi-fiber dental floss of the present invention include a vast array of active and inactive ingredients containing high solids carriers including aqueous-free, melt emulsions such as described in U.S. Pat. Nos. 4,950,479 and 5,032,387 to Hill et al., are hereby incorporated herein by reference. In addition, the chemotherapeutic preparations disclosed and claimed in U.S. Pat. Nos. 4,911,927 and 5,098,711 to Hill et al. are also hereby incorporated herein by reference.

Chemotherapeutic agents suitable for use as active ingredients in the floss of the present invention include: antimicrobials, antibiotics, antibacterial agents, aspirants, adsorbents, cleaners, abrasives, healants, soothants, oxygenating compounds, anti-plaque and anti-tartar substances, organo-iodine salts, pyrophosphates, carbonates, silicates, phenolics, plant alkaloids, vitamins, quaternary ammonium compounds, fluorides, desensitizing agents, analgesics, etc., and mixtures thereof.

Inactive ingredients include: flavors, buffers, stabilizers, viscosifiers, mouth-feel agents, colorants, humectants, etc., such as those described in U.S. Pat. Nos., 4,911,927 and 5,098,711.

In addition to those preparations which achieve their therapeutic benefits specifically by impacting bodily functions by chemical, biochemical or biological means as do the examples described above, chemotherapeutic preparations are defined herein as including those agents in a dental floss whose mechanism of action is to potentiate or allow the unique properties of the textured, multi-fiber dental floss, without multi-component fibers to operate at its fullest therapeutic function, thus improving on the well known therapeutic effects of standard commercial waxed and unwaxed dental flosses, but without direct biological impact on the oral cavity. In this mode, the present invention comprises bundles of multi-fiber dental floss as described above wherein:

(a) the textured fibers are held in place before use by a chemotherapeutic preparation which allow the "activation", previously described, of the fibers either upon tension and release as shown in FIGS. 1–3 or upon contact with saliva or sulcal fluids, and (b) the "active" chemotherapeutic preparations include water-soluble polymers such as starches, modified starches, polyvinyl pyrrolidone, natural gums and resins, cellulose gums and the like as well as, (c) melt-applicable, thermoplastic of alcohol-soluble polymers such as hydroxy propyl cellulose, polyvinyl alcohols, Gantrez® resins by Allied Chemical, high molecular weight polyethylene glycols, Carbowax®, and high molecular weight surfactants such as the poloxamers and various surfactants such as the poloxamers and various ethoxylated esters such as Span® and Tween® having similar properties.

Specific chemotherapeutic agents suitable for the purposes of the present invention include: sodium fluoride, stannous fluoride, sodium monofluorophosphate, zinc chloride, cetylpyridinium, chloride, metronidazole, chlorhexidine, triclosan, tetracycline, aloe-vera, allantoin, thymol, eucalyptol, methyl salicylate, menthol, clove oil, benzocaine, lidocaine, alum, sanguinarine, alexidine, octenidine, penicillin, polymyxin B, vancomycin, kanamycin, erythromycin, niddamycin, spiromycin and acemannen.

The following examples provide a synopsis of the improved multi-bundle, multi-fiber dental flosses of the present invention with expanded interstitial space. Several versions of textured, multi-fiber multi-bundle dental flosses are described with the understanding that numerous other bulking means such as described in the various references and patents cited above could be employed to develop various degrees of expanded interstitial space in the multi-fiber bundles, containing varying concentrations of a broad array of chemotherapeutic preparations, with varying degrees of controlled "activation" and splaying.

Each of the dental flosses of the invention, described in detail below, exhibited excellent dental floss integrity, as well as excellent splaying when "activated".

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

The base material for these examples was 130 denier, 34 filament nylon 6.6, which was heated and false twisted to 60–72 twists per inch (tpi) and then heat set. This produced a nominal 100 denier bundle. Two ends of this 100 denier bundle were air entangled in parallel to produce a nominal 200 denier, 68 filament bundle of textured nylon.

The textured 200 denier bundles were then introduced into a dye bath and dyed either green, orange, or neutral (no FDC color). Four ends of the dyed, textured nylon bundles were then twisted from 1.0 tpi to 2.5 tpi. The colors of the finished twisted bundles ranged from solids of each color to stripes of these various color combinations. The resultant nominal 800 denier twisted/dyed bundle was actually 840 denier by weight.

Four different chemotherapeutic preparations were prepared in high solids melt emulsions following the procedure described in U.S. Pat. No. 5,165,913. These preparations are detailed below. These chemotherapeutic preparations/high solids carrier combinations were then added to several multi-bundle, multi-fiber dental flosses under various conditions as described in Examples 1–4 below.

Each of the texturized multi-bundle, multi-fiber dental flosses of the invention exhibited acceptable dental floss integrity with excellent splaying when "activated".

The chemotherapeutic preparation/carrier combinations introduced into the various dental flosses were:

| | Percentage (%) by wt. |
|---|---|
| Formula A: | |
| Poloxamer 407 | 44.4 |
| Polydimethylsiloxane (Dow Corning 1500) | 17.6 |
| Dicalcium phosphate | 13.3 |
| Carrageenan | 13.3 |
| Flavor | 8.9 |

|  | Percentage (%) by wt. |
| --- | --- |
| Saccharin | 2.2 |
| EDTA | 0.2 |
| Propyl Gallate | 0.1 |
|  | 100.0 |

Formula B:

| Poloxamer 407 | 62 |
| --- | --- |
| Hydrogenated Vegetable Oil | 20 |
| Sodium Bicarbonate | 18 |
|  | 100 |

Formula C:

| Poloxamer 407 | 91.74 |
| --- | --- |
| Sodium Fluoride | 1.6 |
| Cetylpyridinium Chloride | 0.6 |
| Domiphen Bromide | 0.06 |
| Hydrogenated Vegetable Oil | 5.0 |
| Carrageenan | 1.0 |
|  | 100 |

Formula D:

| Poloxamer 407 | 87.1 |
| --- | --- |
| Sorbitol | 10.5 |
| Sodium Fluoride | 1.7 |
| Cetylpyridinium Chloride | 0.63 |
| Domiphen Bromide | 0.07 |
|  | 100 |

EXAMPLE 1

When Formula A was introduced into the textured dental floss described above at 1.0 tpi per the general process described in U.S. Pat. No. 4,911,927 where the loading tank was held at 90° C., the compression rollers at 90° C., the slub gap at 0.018", the line speed was 1.6 yd/sec., the roller speed at 1.9 yd/sec, and the infeed godet at 2.0 yd/sec, the resultant load in was 100 mg/yd.

Under the same process conditions standard untextured nylon at 1.5 tpi loaded 50 mg/yd of Formula A. When this standard untextured dental floss was processed with different process conditions, i.e., tank temperature 80° C., slub gap (0.014), line speed 2.0 yd/sec, roller speed 2.4 yd/sec, and line tension 80 to 100 g, the resultant floss load of Formula A was only 40 mg/hg.

EXAMPLE 2

When Formula B was introduced into standard nylon floss at 1.5 tpi as well into as textured dental flosses of the invention at 1.0, 1.5, and 2.5 tpi under various processing conditions, the influence of texturing and twist on the load of the chemotherapeutic preparation was most evident.

In this example, the untextured floss processed with the loading tank and rollers at 90° C., the slub gap at 0.018. The line speed and roller speeds were 2.0 and 2.4 yd/sec respectively. The line tension was 30–100 g. The load was 34 mg/yd.

Textured yarn at 1.0 and 2.5 tpi run at the very same process settings loaded 82 and 42 mg/yd of Formula B, respectively. Textured yarn of 1.5 tpi run at a slightly lower temperature, tank and roller 80° C. and a slightly lower line speed, 1.7 yd/sec with a roller speed of 2.0 yd/sec and a lower line tension, 40–60 g produced a load of 75 mg/yd of Formula B.

EXAMPLE 3

When Formula C was introduced at 1.5 tpi under the following process conditions;Tank 99° C., roller 80° C., gap 0.018", line speed 1.7 yd/sec, roller speed 2.1 yd/sec, and line tension 80–100 g, the load of Formula C into this texturized dental floss was 64 mg/yd.

EXAMPLE 4

When formula D was introduced into textured floss of the invention at 1.6 tpi and into standard floss at 1.6 tpi under the same process conditions, to wit: tank and roller temperatures 97° C. and 80° C. respectively, gap 0.018", line speed and roller speed, 1.7 and 1.9 yd/sec respectively, and line tension 80–100 g, the influence of texturing on the load of chemotherapeutic agents into the floss of the present invention was dramatically demonstrated, i.e., 80 mg/yd for textured floss vs. 34 mg/yd for standard floss.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. An improved method of adding chemotherapeutic preparations to dental floss containing several multi-fiber bundles, comprising:
   expanding the interstitial space between said fibers, and
   introducing said chemotherapeutic preparations into said expanded interstitial space;
   while maintaining dental floss integrity.

2. An improved method of adding chemotherapeutic preparations to dental floss containing several multi-fiber bundles comprising:
   texturizing said multi-fiber bundles, and
   introducing said chemotherapeutic preparations into said texturized multi-fiber bundles,
   while maintaining dental floss integrity.

3. An improved method of adding chemotherapeutic preparations to dental floss containing several multi-fiber bundles comprising:
   treating said multi-fiber bundles with texturizing means selected from the group consisting of:
      false twist,
      air jet, and
      stuffer box,
   and introducing said chemotherapeutic preparations into said textured multi-fiber bundles;
   while maintaining dental floss integrity.

4. An improved method of adding chemotherapeutic preparations to dental floss containing several multi-fiber bundles comprising:
   A. texturizing said multi-fiber bundles,
   B. air entangling said texturized multi-fiber bundles,
   C. twisting said air entangled multi-fiber bundles,
   D. repetitively spreading said multi-fibers and introducing said chemotherapeutic preparations into the space around said fibers, and
   E. returning said fibers to their pre-spread twist, such that from between about 20 and about 200 mg of said chemotherapeutic preparation is contained in one yard of said floss.

5. The method according to claim 1, 2, 3, or 4, wherein said dental floss contains several multi-fiber bundles with between about 100 and about 800 filaments, and with a denier between about 300 and about 1200.

6. The method according to claim 4, wherein spreading of said fibers is achieved by passing the floss: (a) over a series of flat surfaces under tension and (b) through compressing means in a sequential repetitious manner.

7. The method according to claim 6, wherein said chemotherapeutic preparation is introduced into the spaces around said spread fibers while passing over said flat surfaces and through said compressing means.

8. The method according to claim 1, 2, 3, or 4, wherein said chemotherapeutic preparations comprise a high solids melt-emulsion carrier and one or more additive substances selected from the group consisting of healants, soothants, oxygenating compounds, anti-plaque, anti-tartar substances, antibacterial agents, acemannen, aspirants, adsorbents, and cleaners.

9. The method according to claim 1, 2, 3, or 4, wherein the multi-fiber bundles with expanded interstitial space is dyed and heat set.

10. The method according to claim 1, 2, 3, or 4, wherein the chemotherapeutic preparation introduced into said expanded interstitial space functions as an absorbent of materials selected from the group consisting of sulcal fluids, infection discharges, toxins, bacteria laden fluids, blood, and bacterial debris.

11. The method according to claim 1, 2, 3, or 4, wherein the chemotherapeutic preparation introduced into said expanded interstitial space functions to chemically aspirate bacteria laden fluids and toxins in interproximal and subgingival areas.

12. A method of treating interproximal and subgingival areas of the oral cavity with various site specific chemotherapeutic preparations comprising:
   a. activating dental floss comprising several multi-fiber bundles having expanded interstitial space between said fibers, wherein said expanded space contains one or more chemotherapeutic preparations;
   b. working said activated dental floss between teeth and subgingivally to mechanically clean said areas while releasing said chemotherapeutic preparation; and
   c. removing the spent multi-fiber dental floss from the interproximal and/or subgingival area along with entrapped food particles, debris, loosened plaque and tartar.

13. The method according to claim 12, wherein said chemotherapeutic preparation comprise a high solids melt-emulsion carrier and one or more additive substances selected from the group consisting of healants, soothants, oxygenating compounds, anti-plaque substances, anti-tartar substances, antibacterial agents, acemannen, aspirants, adsorbents, and cleaners.

14. The method according to claim 12, wherein said bundles of multi-fiber dental floss are texturized prior to introducing chemotherapeutic preparations into the resulting expanded interstitial space.

15. The method according to claim 12, wherein said bundles of multi-fibers are texturized, air entangled and twisted prior to the introduction of one or more chemotherapeutic preparations.

16. The method according to claim 15, wherein the twisting of the fibers is at about 1 twist per inch.

17. The method according to claim 15, wherein the multi-fiber, expanded interstitial space dental floss is dyed and heat set prior to the introduction of one or more chemotherapeutic preparations.

18. A method of treating infected, diseased, bleeding, or traumatized interproximal and subgingival areas of gums with site specific chemotherapeutic preparations comprising:
   a. activating a dental floss comprising several multi-fiber bundles, containing cleaners and adsorbents; working said activated dental floss interproximally and subgingivally to release said cleaners and adsorbents and removing the spent dental floss along with any entrapped debris, bacteria, bacteria ladened fluids and toxins;
   b. activating a second dental floss comprising several multi-fiber bundles containing chemical aspirants, working said activated floss subgingivally and interproximally to aspirate the sites of infection, disease or bleeding, and removing the spent dental floss along with any entrapped debris, aspirated bacteria, bacteria ladened fluids and toxins; and
   c. activating a third dental floss comprising several multi-fiber bundles containing appropriate chemotherapeutic preparations selected from the group consisting of: antimicrobials, antibiotics, healants, soothants, oxygenating compounds and antibacterial agents, working said activated floss subgingivally and interproximally into the sites of infection, disease or bleeding, and removing the spent dental floss leaving behind an effective amount of an appropriate chemotherapeutic preparation selected from the group consisting of antimicrobials, antibiotics, healants, soothants, oxygenating compounds and antibacterial agents.

19. An improved dental floss consisting of several multi-fiber bundles wherein said bundles of fibers have undergone bulking, said floss further containing one or more chemotherapeutic preparations; and wherein the texturized multi-fiber bundles are air entangled and twisted prior to the introduction of the chemotherapeutic preparations; the improvement consisting of
   said floss having two physical states; a contracted form and an expanded or bulkier form, wherein expansion of the contracted floss to the bulkier physical state is achieved by release of tension applied to the contracted floss during use thereof.

20. An improved dental floss consisting of several multi-fiber bundles wherein said bundles of fibers have undergone texturizing, said floss further containing one or more chemotherapeutic preparations; and wherein the texturized multi-fiber bundles are air entangled and twisted prior to the introduction of the chemotherapeutic preparations; the improvement consisting of
   said floss having two physical states; a contracted form and an expanded or bulkier form, wherein expansion of the contracted floss to the bulkier physical state is achieved by release of tension applied to the contracted floss during use thereof.

21. The improved dental floss according to claim 19, wherein the fiber bundles are twisted at about 1 twist per inch.

22. The improved dental floss according to claim 19, wherein said chemotherapeutic preparation is contained in a carrier.

23. The improved dental floss according to claim 19, wherein said carrier is an aqueous-free high solids melt emulsion.

24. The improved dental floss according to claim 19, wherein said chemotherapeutic preparation comprises one or more additive substances in a high solids melt emulsion carrier, and wherein said additive substance is selected from the group consisting of healants, soothants, oxygenating compounds, anti-plaque, anti-tartar substances, antibacterial agents, acemannen, aspirants, adsorbents, and cleaners; and wherein the texturized multi-fiber bundles are air entangled and twisted prior to the introduction of the chemotherapeutic preparations.

25. An improved dental floss consisting of several multi-fiber bundles that have undergone texturizing containing a chemotherapeutic preparation selected from the group consisting of sodium fluoride, stannous fluoride, sodium monofluorophosphate, zinc chloride, cetyl pyridinium chloride, metronidazole, chlorhexidine, triclosan, benzocaine and lidocaine, suitable for ameliorating sulcal fluids, infection discharges, bacterial laden fluids, blood, debris and toxins; and wherein the texturized multi-fiber bundles are air entangled and twisted prior to the introduction of the chemotherapeutic preparations, the improvement consisting of
said floss having two physical states; a contracted form and an expanded or bulkier form, wherein expansion of the contracted floss to the bulkier physical state is achieved by release of tension applied to the contracted floss during use thereof.

26. An improved dental floss consisting of several texturized, multi-fiber bundles containing a chemotherapeutic preparation selected from the group consisting of tetracycline, penicillin, polymyxin B, vancomycin, kanamycin, erythromycin, niddamycin, and spiromycin, suitable for ameliorating bacteria laden fluids, toxins, and sites of infection in interproximal and subgingival areas; and
wherein the texturized multi-fiber bundles are air entangled and twisted prior to the introduction of the chemotherapeutic preparations;
the improvement consisting of
said floss having two physical states; a contracted form and an expanded or bulkier form, wherein expansion of the contracted floss to the bulkier physical state is achieved by release of tension applied to the contracted floss during use thereof.

27. An improved dental floss consisting of several texturized, multi-fiber bundles containing a chemotherapeutic preparation having the propensity to expand dramatically during use to release said chemotherapeutic preparation along with improved splaying; and
wherein the texturized multi-fiber bundles are air entangled and twisted prior to the introduction of the chemotherapeutic preparations;
the improvement consisting of
said floss having two physical states; a contracted form and an expanded or bulker form, wherein expansion of the contracted floss to the bulkier physical state is achieved by release of tension applied to the contracted floss during use thereof.

28. The method according to claim 1, wherein the multi-fiber bundles comprise bi-polymer fibers.

29. The method according to claim 1, wherein from 1 to 6 of the multi-fiber bundles contain specific functionality fibers.

30. The method according to claim 1, wherein said chemotherapeutic preparation is an activation chemotherapeutic preparation.

31. The method according to claim 12, wherein the multi-fiber bundles comprise bi-polymer fibers.

32. The method according to claim 12, wherein said chemotherapeutic preparation is an activation chemotherapeutic preparation.

33. The improved dental floss according to claim 18, wherein the multi-fiber bundles comprise bi-polymer fibers.

34. A method of treating gum disease comprising flossing the interproximal and subgingival areas of infection with a microbial ecology altering dental floss consisting of several multi-fiber bundles which have undergone bulking, said floss further containing a chemotherapeutic preparation useful against infection; and wherein the texturized multi-fiber bundles are air entangled and twisted prior to the introduction of the chemotherapeutic preparations and wherein, said floss expands to a bulkier state upon release of tension applied to the floss during use thereof.

35. A method of treating interproximal caries comprising flossing the interproximal cavity prone areas with a multi-fiber, multi-bundle dental floss containing a fluoride containing anti-caries preparation, wherein said bundles of fibers have undergone texturizing; and wherein the texturized multi-fiber bundles are air entangled and twisted prior to the introduction of the chemotherapeutic preparations and wherein, said floss expands to a bulkier state upon release of tension applied to the floss during use thereof.

36. An improved method of adding chemotherapeutic preparations to dental floss containing several multi-fiber bundles comprising;
texturizing said multi-fiber bundles with texturizing means selected from the group consisting of stretch, modified stretch and bulk means, and introducing said chemotherapeutic preparations into said textured multi-fiber bundles, while maintaining dental floss integrity.

37. A method according to claim 36, wherein said chemotherapeutic preparations comprise active ingredients selected from the group consisting of antimicrobials, antibiotics, antibacterial agents, organo-iodine salts, pyrophosphates, carbonates, silicates, phenolics, quaternary ammonium compounds, analgesics, and mixtures thereof.

38. An improved dental floss according to claim 20, wherein said texturizing is selected from the group consisting of stretch, modified stretch and bulk means.

39. An improved dental floss according to claim 19, wherein said chemotherapeutic preparations comprise active ingredients selected from the group consisting of antimicrobials, antibiotics, antibacterial agents, organo-iodine salts, pyrophosphates, carbonates, silicates, phenolics, quaternary ammonium compounds, analgesics, and mixtures thereof.

40. The method of claim 8, wherein the additive substance is selected from the group consisting of sodium fluoride, stannous fluoride, sodium monofluorophosphate, zinc chloride, cetyl pyridinium chloride, metronidazole, chlorhexidine, organo iodine salts, triclosan, tetracycline, aloe-vera, allantoin, thymol, eucalyptol, methyl salicylate, menthol, clove oil, benzocaine, lidocaine, pyrophosphates, carbonates, silicates, alum, quaternary ammonium compounds, phenolic compounds, plant alkaloids, sanguinarine, alexidine, octenidine, penicillin, polymyxin B, vancomycin, kanamycin, erythromycin, niddamycin, spiromycin.

41. The method of claim 13, wherein the additive substance is selected from the group consisting of sodium fluoride, stannous fluoride, sodium monofluorophosphate, zinc chloride, cetyl pyridinium chloride, metronidazole, chlorhexidine, organo iodine salts, triclosan, tetracycline, aloe-vera, allantoin, thymol, eucalyptol, methyl salicylate, menthol, clove oil, benzocaine, lidocaine, pyrophosphates, carbonates, silicates, alum, quaternary ammonium compounds, phenolic compounds, plant alkaloids, sanguinarine, alexidine, octenidine, penicillin, polymyxin B, vancomycin, kanamycin, erythromycin, niddamycin, spiromycin.

42. The improved dental floss according to claim 24, wherein the additive substance is selected from the group consisting of sodium fluoride, stannous fluoride, sodium monofluorophosphate, zinc chloride, cetyl pyridinium chloride, metronidazole, chlorhexidine, organo iodine salts, triclosan, tetracycline, aloe-vera, allantoin, thymol, eucalyptol, methyl salicylate, menthol, clove oil, benzocaine, lidocaine, pyrophosphates, carbonates, silicates, alum, quaternary ammonium compounds, phenolic compounds, plant alkaloids, sanguinarine, alexidine, octenidine, penicillin, polymyxin B, vancomycin, kanamycin, erythromycin, niddamycin, spiromycin.

43. A method according to claim 36, wherein said chemotherapeutic preparations comprise active ingredients selected from the group consisting of healants, soothants, plant alkaloids, vitamins, fluorides, desensitizing agents, and mixtures thereof.

44. A method according to claim 36, wherein said chemotherapeutic preparations comprise active ingredients selected from the group consisting of aspirants, adsorbents, cleaners, abrasives, oxygenating compounds, anti-plaque and anti-tartar substances, and mixtures thereof.

45. An improved dental floss according to claim 19, wherein said chemotherapeutic preparations comprise active ingredients selected from the group consisting of aspirants, adsorbents, cleaners, abrasives, oxygenating compounds, anti-plaque and anti-tartar substances, fluorides, desensitizing agents, and mixtures thereof.

46. An improved dental floss according to claim 19, wherein said chemotherapeutic preparations comprise active ingredients selected from the group consisting of healants, soothants, plant alkaloids, vitamins, and mixtures thereof.

* * * * *